US009562240B2

(12) United States Patent
Choi et al.

(10) Patent No.: US 9,562,240 B2
(45) Date of Patent: Feb. 7, 2017

(54) PROCESS OF BIOLOGICALLY PRODUCING AROMATIC CARBOXYLIC ACID AND DERIVATIVE THEREOF

(71) Applicant: Samsung Electronics Co., Ltd., Suwon-si, Gyeonggi-do (KR)

(72) Inventors: Won Jae Choi, Seongnam-si (KR); Jin Ho Ahn, Seongnam-si (KR); Jong Won Byun, Suwon-si (KR); Young Wan Ha, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 146 days.

(21) Appl. No.: 14/091,420

(22) Filed: Nov. 27, 2013

(65) Prior Publication Data

US 2014/0154761 A1 Jun. 5, 2014

(30) Foreign Application Priority Data

Nov. 30, 2012 (KR) ........................ 10-2012-0138373

(51) Int. Cl.
*C12P 7/40* (2006.01)
*C12P 7/44* (2006.01)
*C12P 7/42* (2006.01)

(52) U.S. Cl.
CPC ... *C12P 7/40* (2013.01); *C12P 7/42* (2013.01)

(58) Field of Classification Search
CPC .................. C12P 7/40; C12P 7/42; C12P 7/44
USPC ......................................... 435/136, 142, 146
See application file for complete search history.

(56) References Cited

U.S. PATENT DOCUMENTS

| 2003/0167511 A1 | 9/2003 | Narbad et al. |
| 2012/0202272 A1 | 8/2012 | Chatterjee et al. |
| 2013/0130345 A1 | 5/2013 | Thai et al. |
| 2014/0155570 A1 | 6/2014 | Choi et al. |

FOREIGN PATENT DOCUMENTS

| CA | 2389138 A1 | 5/2001 |
| EP | 2738261 A2 | 6/2014 |
| GB | 1117498 A | 6/1968 |
| JP | 06-078780 A | 3/1994 |
| JP | 2004-215586 A | 8/2004 |
| WO | WO 01/31047 A2 | 5/2001 |
| WO | WO 2012/006039 A2 | 1/2012 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Gibson et al. J. Bacteriology 1977, pp. 634-642.*
Arceo et al., "A Direct, Biomass-Based Synthesis of Benzoic Acid: Formic Acid-Mediated Deoxygenation of the Glucose-Derived Materials Quinic Acid and Shikimic Acid" *ChemSusChem* 3(7): 811-813 (2010).
Barker et al., "Microbial Synthesis of p-Hydroxybenzoic Acid from Glucose" *Biotechnology and Bioengineering* 76(4): 376-390 (Dec. 2001).
Lupa et al., "Properties of the reversible nonoxidative vanillate/4-hydroxybenzoate decarboxylase from *Bacillus subtilis*" *Can. J. Microbiol.* 54: 75-81 (2008).
Ritzer et al., "Hydroxycarboxylic Acids, Aromatic" *Ullmann's Encyclopedia of Industrial Chemistry* 18: 493-501 (2012).
Hirai et al., "Regioselective carboxylation of aromatic compounds using cyclodextrin as mediator", *Reactive and Functional Polymers*, 67(11): 1115-1128 (2007).
Sircar et al., "Characterization of p-hydroxybenzaldehyde dehydrogenase, the final enzyme of p-hydroxybenzoic acid biosynthesis in hairy roots of *Daucus carota*", *Acta Physiologiae Plantarum*, 33:2019-2024 (2011).
Traynard, "Oxidation of some substituted hydroxybenzaldehydes", pp. 2021 (1957) (CAPLUS Abstract XP-002727808 only).
EPO Extended Search Report in Application No. 13195046.1 dated Aug. 11, 2014.

* cited by examiner

*Primary Examiner* — Robert Mondesi
*Assistant Examiner* — MD. Younus Meah
(74) *Attorney, Agent, or Firm* — Leydig, Voit & Mayer, Ltd.

(57) ABSTRACT

A method of biologically producing an aromatic carboxylic acid by contacting a substrate containing an aromatic carboxylic acid having a para-hydroxy group with a biocatalyst that removes the para-hydroxy group.

12 Claims, 2 Drawing Sheets

1. 3,4-dihydroxybenzoic acid, 2. p-hydroxybenzoic acid, 3. vanillic acid, 4. p-hydroxybenzaldehyde, 5. syringic acid, 6. vanillin, 7. coniferyl alcohol, 8. syringaldehyde, 9. guaiacol, 10. 2,6-dimethoxyphenl, 11. benzoic acid, 12. 2,6-dimethoxy-4-methylphenol, 13. 2-methyoxy-4-methylphenol

PROCESS OF BIOLOGICALLY PRODUCING AROMATIC CARBOXYLIC ACID AND DERIVATIVE THEREOF

CROSS-REFERENCE TO RELATED APPLICATIONS

This application claims the benefit of Korean Patent Application No. 10-2012-0138373, filed on Nov. 30, 2012, in the Korean Intellectual Property Office, the entire disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 27,599 Byte ASCII (Text) file named "715455_ST25.TXT," created on Nov. 19, 2013.

BACKGROUND OF THE INVENTION

Field of the Invention

The present invention relates to the biological production of aromatic carboxylic acid and its derivatives. More particularly, the present invention relates to a process of biologically producing aromatic carboxylic acid and its derivatives by degrading lignin through chemical or biological conversion and biologically converting the lignin breakdown product into aromatic carboxylic acid or derivatives thereof.

Description of the Related Art

Today's chemical industry is highly dependent on crude oil as a feedstock to produce almost every commodity chemical or material. Aromatic hydrocarbons are among the most important raw materials in the chemical industry, and are obtained exclusively from fossil resources.

Benzoic acid, which is structurally the simplest among aromatic carboxylic acids, is used as intermediate for the manufacture of caprolactam, terephthalic acid, dyes and perfumes, and as a preservative in food and drugs. In addition, oxidative decarboxylation of benzoic acid is an important route in the manufacturing of phenol. Phenol is used mainly in the production of phenolic resins and bisphenol A.

Benzoic acid is prepared industrially by liquid-phase oxidation of toluene in the presence of cobalt or manganese naphthenic acid catalysts. However, increases in crude oil prices results in high manufacturing costs for aromatic raw materials, such as toluene. Furthermore, conventional petroleum-based benzoic acid production is recognized as nonrenewable and generates a lot of greenhouse gases. In this context, there is an increasing demand for an alternative route for benzoic acid production via industrial biotechnology using renewable biomass as feedstock.

WO 2012006039 discloses a process for producing a renewable benzoic acid, comprising dehydrogenating cyclic monoterpene into p-cymene, followed by contacting p-cymene with benzene to yield toluene, and oxidizing toluene into renewable benzoic acid. However, the oxidation of toluene into benzoic acid is carried out using a conventional chemical conversion process.

Elena et al. describes the synthesis of benzoic acid by formic acid-mediated didehydroxylation (Elena et. al., ChemSusChem. 3(7):811-3). However, the final product undergoes sublimation deposition during distillation. To avoid this problem, the usable solvents are limited.

There is, therefore, a strong need for a biological process of producing benzoic acid from renewable biomass.

SUMMARY OF THE INVENTION

An embodiment of the present invention provides a biological process of producing aromatic carboxylic acid or its derivative with high specificity, compared to chemical processes.

Another embodiment provides a biological process of producing aromatic carboxylic acid and its derivative in an environment-friendly manner from a lignin degradation product which is degraded economically and effectively from lignin.

A further embodiment pertains to a biological process of producing benzoic acid or a derivative thereof. More particularly, benzoic acid or a derivative thereof can be produced biologically from an aromatic carboxylic acid or a derivative thereof.

Still a further embodiment provides the production of benzoic acid or a derivative thereof from lignin, a recyclable biomass. In this regard, lignin is chemically and/or biologically degraded to give lignin breakdown products including aromatic monomers, followed by biological conversion of the breakdown products into benzoic acid or a derivative thereof.

Focusing on the synthesis of benzoic acid or a derivative thereof from non-edible biomass, the present invention is configured to chemically or biologically degrade lignin, an inexpensive raw material, into aromatic monomers and to chemically or biologically convert the aromatic monomers into benzoic acid, thus eliminating dependence on petrochemical materials.

By using a biological process in which a substrate including an aromatic carboxylic acid having a p-hydroxy group, or a derivative thereof is contacted with a biocatalyst having an activity to remove the p-hydroxy group, an embodiment of the present invention allows benzoic acid or a derivative thereof to be produced in an environment-friendly manner and at higher specificity, compared to a chemical process.

An embodiment provides the production of benzoic acid or a derivative thereof from lignin. In this regard, lignin may be degraded to give lignin breakdown products including aromatic monomers, followed by biological conversion of the breakdown products into benzoic acid or a derivative thereof.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
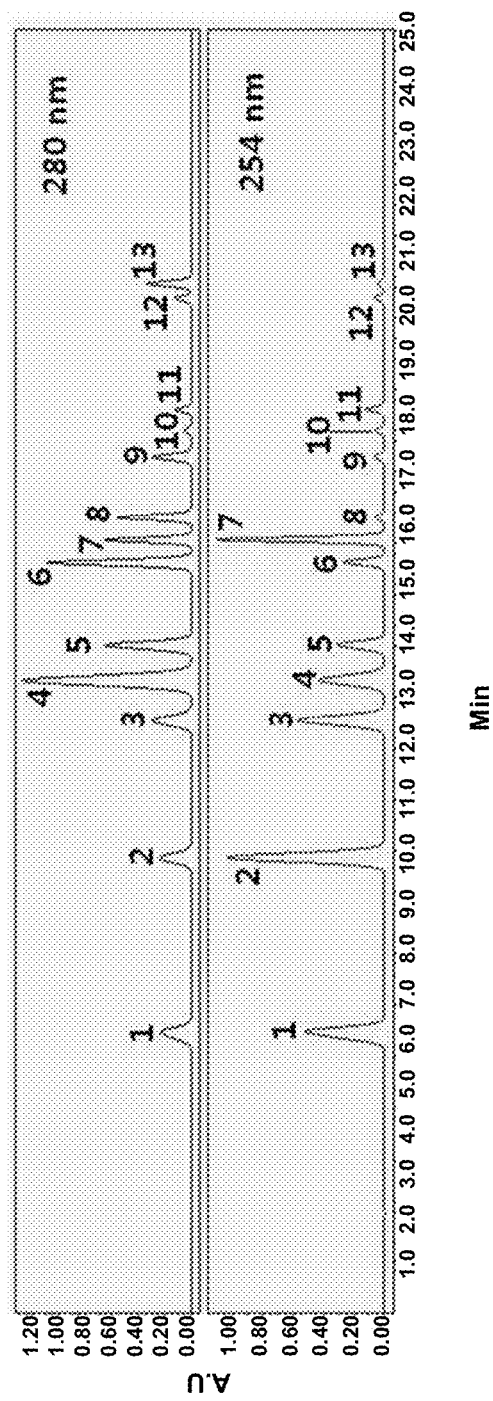
FIG. 1 shows HPLC chromatograms of a standard solution of enzyme reaction intermediates comprising p-hydroxybenzoic acid, benzoic acid and terephthalic acid, as quantitatively measured by Waters e2695 HPLC and Waters 2489 UV/VIS (253 nm, 280 nm) detector.

An embodiment of the present invention addresses a process of biologically producing an aromatic carboxylic acid represented by the following Chemical Formula 1 or a derivative thereof, comprising contacting a substrate including an aromatic carboxylic acid having a p-hydroxy group, represented by the following Chemical Formula 2, with a biocatalyst having a catalytic activity to remove a hydroxy group at p-position, as illustrated in the following Reaction Scheme 1.

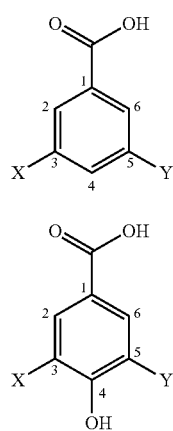

[Chemical Formula 1]

[Chemical Formula 2]

wherein, X and Y, which may be the same or different, are independently hydrogen, hydroxy, or C1-C4 alkoxy. The C1-C4 alkoxy may be linear or branched, and is preferably methoxy or ethoxy.

The aromatic carboxylic acid of Chemical Formula 1 can be synthesized from a substrate including an aromatic carboxylic acid having a p-hydroxy group in the presence of a biocatalyst capable of removing a p-hydroxy group.

Preferable among the compounds of Chemical Formula 1 are benzoic acid, m-hydroxybenzoic acid, 3,5-dihydroxybenzoic acid, 3-methoxybenzoic acid, and 3,5-dimethoxybenzoic acid.

The compound represented by Chemical Formula 2 corresponds to the compound of Chemical Formula 1, and can be produced using a petrochemical process or a biological process. For example, it may be produced using a commercial chemical process based on the Kolbe-Schmitt reaction, or through an aromatic amino acid biosynthesis pathway (Edwin Ritzer and Rudolf Sundermann "Hydroxycarboxylic Acids, Aromatic" in Ullmann's Encyclopedia of Industrial Chemistry 2002, Wiley-VCH, Weinheim; Biotechnol Bioeng. 2001 December; 76(4):376-90). Alternatively, the compound of Chemical Formula 2 may be obtained from a breakdown product of lignin after chemical and/or biological degradation, or from a compound of Chemical Formula 3 as will be further explained, below. The degradation of lignin may be carried out using at least one selected from the group consisting of pyrolysis, gasification, hydrogenolysis, acidolysis, alkaline lysis, chemical oxidation, hydrolysis under supercritical conditions, and enzymatic degradation. Preferred examples of the compound of Chemical Formula 2 include 4-hydroxybenzoic acid, 3,4-dihydroxybenzoic acid, 4,5-dihydroxybenzoic acid, 3,4,5-trihydroxybenzoic acid, 3-methoxy-4-hydroxybenzoic acid, 4-hydroxy-5-methoxybenzoic acid, and 3,5-dimethoxy-4-hydroxybenzoic acid.

In one embodiment, the aromatic carboxylic acid having a p-hydroxy group of Chemical Formula 2 may be prepared from an aromatic aldehyde having a p-hydroxy group of Chemical Formula 3 by chemical oxidation or biocatalytic oxidation.

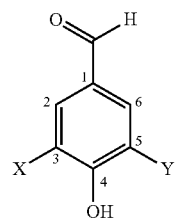

[Chemical Formula 3]

wherein, X and Y, which may be the same or different, are independently hydrogen, hydroxy, or C1-C4 alkoxy. The C1-C4 alkoxy may be linear or branched, with preference for methoxy or ethoxy. Representative of the compound of Chemical Formula 3 are p-hydroxybenzaldehyde, vanillin, and syringaldehyde.

The compound of Chemical Formula 3 which corresponds to the compound of Chemical Formula 2 may be produced using a petrochemical process or a biological process. For example, it may be obtained by chemically or biologically degrading lignin. In one embodiment, thus, the process of the present invention may further comprise degrading lignin to provide a breakdown product of lignin including the aromatic aldehyde having a p-hydroxy group of Chemical Formula 3; and oxidizing the breakdown product of lignin to convert the aromatic aldehyde having a p-hydroxy group into an aromatic carboxylic acid having p-hydroxy group of Chemical Formula 2.

A process of producing a benzoic acid or a derivative thereof from an aromatic aldehyde in accordance with an embodiment of the present invention is illustrated in Reaction Scheme 1. Briefly, an aromatic aldehyde having a p-hydroxy group of Chemical Formula 3 is chemically or biologically oxidized into an aromatic carboxylic acid having a p-hydroxy group of Chemical Formula 2, followed by biological removal of the p-hydroxy group to give a p-hydroxy-free aromatic carboxylic acid, that is, benzoic acid or a derivative thereof.

[Reaction Scheme 1]

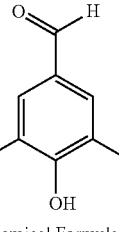
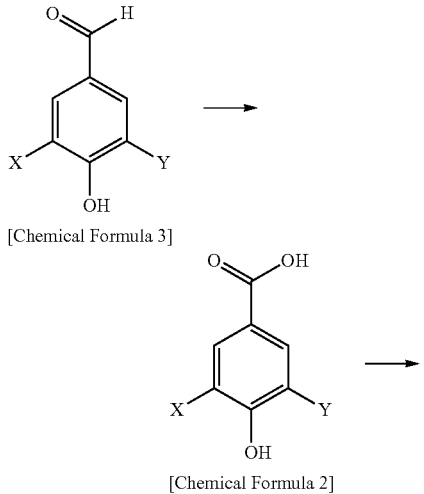
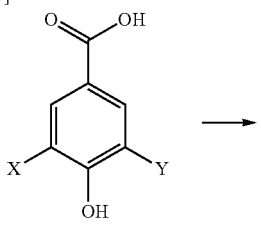

[Chemical Formula 3]

[Chemical Formula 2]

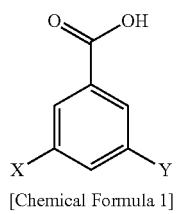

[Chemical Formula 1]

When X and Y in the compounds of Chemical Formulas 1 to 3 are not simultaneously a hydrogen substituent, the process of the present invention may further comprise removing at least one substituent selected from the group consisting of hydroxy and C1-C4 alkoxy at either or both positions 3' and 5' of the benzene ring. The removal of the substituent may be carried out prior to, simultaneously with, or after each step of Reaction Scheme 1.

According to one embodiment, when X and Y are not simultaneously hydrogen in Chemical Formula 2, the process of the present invention may further comprises contacting the substrate with a biocatalyst having the catalytic activity to remove a substituent selected from the group consisting of hydroxy and C1-C4 alkoxy at either or both of positions 3 and 5 on the benzene ring before, simultaneously with, or after contacting with the biocatalyst having the catalytic activity to remove a hydroxy group at p-position. For example, when X and Y in Chemical Formula 2 are hydrogen and methoxy, respectively, the hydroxyl group at p-position and the methoxy of Y may be removed to give a benzoic acid.

According to another embodiment, when X and Y are not simultaneously hydrogen in Chemical Formula 3, the process of the present invention may further comprises contacting the substrate with a biocatalyst having the catalytic activity to remove a substituent selected from the group consisting of hydroxy and C1-C4 alkoxy at either or both of positions 3 and 5 on the benzene ring before, simultaneously with, or after the oxidation.

The process illustrated in Reaction Scheme 1 may be implemented in the presence of a biocatalyst having a catalytic activity to remove p-hydroxy from the aromatic carboxylic acid having a p-hydroxy group of Chemical Formula 2, and a biocatalyst having a catalytic activity to remove at least one substituent selected from the group consisting of hydroxy and C1-C4 alkoxy at either or both 3- and 5-positions on the aromatic carboxylic acid.

So long as it can remove a hydroxy group at para-position of the benzene ring from the aromatic carboxylic acid having a p-hydroxy group of Chemical Formula 2 when brought into contact with a substrate including the aromatic carboxylic acid, any enzyme may be used in the present invention. The enzyme may be selected from the group consisting of, but not limited to, bile-acid 7-alpha-dehydroxylase (EC 1.17.99.5), 4-hydroxybenzoyl-CoA reductase (EC 1.3.7.9), 3-dehydroquinate hydro-lyase (EC 4.2.1.10), aldos-2-ulose dehydratase ((EC 4.2.1.110), Biochim Biophys Acta. 2005, 1723(1-3):63-73), o-succinylbenzoate synthase (EC 4.2.1.113), 3-dehydroshikimate hydro-lyase (EC 4.2.1.118), prephenate hydro-lyase (EC 4.2.1.51), arogenate dehydratase (EC 4.2.1.91), scytalone 7,8-hydro-lyase (EC 4.2.1.94), and 16α-hydroxyprogesterone hydro-lyase ((EC 4.2.1.98), J Steroid Biochem Mol. Biol. 1991, 38(2):257-63).

Examples of the biocatalyst having the activity to remove p-hydroxy from the aromatic hydroxycarboxylic acid of Chemical Formula 2 include Gene Ontology Numbers GO:0047769, GO:0004664, GO:0046565, GO:0003855, GO:0030411, GO:0033991, GO:0043748, GO:0047455, GO:0018525, and GO:0033792.

The enzymes are summarized, together with their genes, in Table 1, below.

TABLE 1

| Enzyme | Gene | GenBank Accession No. | Microbial Source |
|---|---|---|---|
| bile-acid 7-alpha-dehydroxylase | baiA2 | AAB61150.1 | *Eubacterium* sp. (strain VPI 12708) |
| 4-hydroxybenzoyl-CoA reductase | hcrA | CAA05038.1 | *Thauera aromatica* |
| 3-dehydroquinate hydro-lyase | aroD | ACR61804.1 | *Escherichia coli* |
| o-succinylbenzoate synthase | menC | AAA71917.1 | *Escherichia coli* |
| 3-dehydroshikimate hydro-lyase | qa-4 | CAA32750.1 | *Neurospora crassa* |
| prephenate hydro-lyase | PHA2 | DAA10245.1 | *Saccharomyces cerevisiae* |
| arogenate dehydratase | Bphy | ACC72194.1 | *Burkholderia phymatum* |
| scytalone 7,8-hydro-lyase | SDH1 | BAA34046.1 | *Magnaporthe oryzae* |

For instance, prephenate hydro-lyase (PHA2) is capable of removing the hydroxy group at para-position of the compound of Chemical Formula 2 to afford the compound of Chemical Formula 1. The prephenate hydro-lyase useful in the present invention may have an amino acid sequence (PHA2) as set forth in SEQ ID NO: 2.

The catalyst which can remove at least one substituent selected form hydroxy and C1-C4 alkoxy at position 3' and/or 5' of the benzene ring from the aromatic carboxylic acid may be an enzyme selected from the group consisting of anthranilate synthase (EC 4.1.3.27), aminodeoxychorismate lyase (EC 4.1.3.38), chorismate lyase (EC 4.1.3.40), 3-dehydroquinate hydro-lyase (EC 4.2.1.10), 3-dehydroshikimate hydro-lyase (EC 4.2.1.118), prephenate hydro-lyase (EC 4.2.1.51), 5-O-(1-carboxyvinyl)-3-phosphoshikimate phosphate-lyase (EC 4.2.3.5), isochorismate lyase (EC 4.2.99.21), and hydroxyphenylpyruvate synthase (EC 5.4.99.5), or a microorganism producing the enzyme, a lysate of the microorganism, or an extract from the microorganism cell lysate. The aminodeoxychorismate lyase (ADC lyase) may have an amino acid sequence as set forth in SEQ ID NO: 4.

Examples of the catalyst having the activity to remove at least one substituent selected form hydroxy and C1-C4 alkoxy at position 3' and/or 5' of the benzene ring from the aromatic carboxylic acid include Gene Ontology Numbers (GO Nos.) GO:004049, GO:005950, GO:004107, GO:008813, GO:0046565, GO:0043904, GO:008696, GO:004664, GO:003855, and GO:004106.

The enzymes are summarized, together with their genes, in Table 2, below.

TABLE 2

| Enzyme | Gene | GenBank Accession No. | Microbial Source |
|---|---|---|---|
| Anthranilate synthase | TRP2 | AAA35175.1 | *Saccharomyces cerevisiae* |
| Aminodeoxychorismate lyase | ABZ2 | DAA10190.1 | *Saccharomyces cerevisiae* |

TABLE 2-continued

| Enzyme | Gene | GenBank Accession No. | Microbial Source |
|---|---|---|---|
| Chorismate lyase | ubiC | CAA47181.1 | Escherichia coli |
| 3-Dehydroquinate hydro-lyase | aroD | ACR61804.1 | Escherichia coli |
| 3-Dehydroshikimate hydro-lyase | quiC | AAC37159.1 | Acinetobacter sp. (strain ADP1) |
| Prephenate hydro-lyase | pheA | AAA22507.1 | Bacillus subtilis |
| 5-O-(1-Carboxyvinyl)-3-phosphoshikimate phosphate lyase | aroC | AAA23487.1 | Escherichia coli |
| Isochorismate lyase | entB | AAA16102.1 | Escherichia coli |
| hydroxyphenylpyruvate synthase | aroH | ADE84133.1 | Rhodobacter capsulatus |

An enzyme may act on various substrates, and even on unknown substrates. In addition, an enzyme differs in activity from one substrate to another, and can be changed in activity or specificity for a certain substrate through modification, such as mutation or directed evolution. Like this, the enzymes of the present invention can be changed in substrate specificity or enhanced in activity using protein evolution technology so as to increase the productivity of the products.

As mentioned above, the enzymes, microorganisms as enzyme sources, lysates of the microorganisms, or extracts from the microorganism cell lysates may be used as the biocatalyst of the present invention. Contacting the substrate with the biocatalyst may be performed under suitable conditions to produce the product by bringing the substrate into contact with an enzyme, a microorganism containing the enzyme, a lysate of the microorganism, or an extract from the microorganism cell lysate, or culturing the microorganism in a medium containing the substrate.

The enzymatic reaction in each step of the present invention may be achieved by contacting the substrate with a proper enzyme or a microorganism containing the enzyme, or culturing the microorganism in a medium containing the substrate. The enzymatic reaction may be done at a pH of from 5.0 to 10.0, with an optimal pH dependent on the enzyme used. In addition, the enzymatic reaction may be done at a temperature of from 25° C. to 50° C., with the optimal temperature depending on the enzyme employed. In a preferred embodiment of the present invention, conversion from aromatic aldehyde to aromatic carboxylic acid is executed at 30° C.~37° C.

In a further embodiment of the present invention, the microorganism used in each step of the present invention may be recombinant or of wild-type. A recombinant microorganism might be prepared by introducing a gene encoding the enzyme into a host cell using a recombinant technique.

When a recombinant enzyme is used according to one embodiment of the present invention, the process comprises 1) constructing an expression vector carrying a gene coding for the enzyme; 2) transforming the expression vector into a host cell, followed by culturing the host cell; 3) producing the enzyme from the host cell; and 4) reacting the enzyme with the substrate. The enzyme acting on the substrate may be in a pure or crude form.

Any expression vector that is employed in genetic manipulation could be applied to the construction of the recombinant expression vector for use in producing benzoic acid or a derivative thereof. So long as it is transformed with the recombinant expression vector to expresses the gene of interest to produce an active enzyme protein, any strain, whether bacterial, fungal, or of yeast, can be used as a host cell in the present invention. Preferred is E. coli.

Focusing on the synthesis of benzoic acid from biomass, the present invention is configured to chemically or biologically degrade lignin into breakdown products from which aromatic carboxylic acid, particularly benzoic acid or a derivative thereof is produced.

Within the scope of the lignin of the present invention are lignin, lignin derivatives, lignin fragments, and lignin-containing material. The term "lignin derivatives," as used herein, is intended to encompass lignin compounds modified by a chemical reaction, such as phenolation, acetylation, etc. The term "lignin fragments" means breakdown products obtained as a result of the chemical or biological degradation of lignin.

Typically, lignin is obtained by separating cellulose and hemicelluloses in the biorefinery or pulping process. There are various types of lignin including kraft lignin (alkaline lignin), dealkaline lignin, hydrolytic lignin, organosolv lignin, and sodium lignin sulfonate, according to production process. As a by-product from the lignocelluloses bioethanol process, lignin can be also used Lignin is an aromatic polymer surrounding microfibers, forming a resinous structure in which phenylpropanoids, such as coumaryl alcohol, coniferyl alcohol, sinapyl alcohol, etc. serve as structural units, being polymerized via carbon-carbon bonds or carbon-oxygen bonds in a haphazard manner.

The degradation of lignin may be biodegradation or physicochemical degradation, the latter being preferred because of higher degradation rate. Biodegradation of lignin may be carried out with enzymes such as peroxidase and laccase. Besides, lignin may be degraded physicochemically. Among the types of physicochemical degradation available for lignin in the present invention are pyrolysis, gasification, hydrogenolysis, acidolysis, alkaline lysis, chemical oxidation, and hydrolysis under supercritical conditions.

In one embodiment, the acidolysis or alkaline lysis of lignin is preferably accomplished by treatment with $H_2SO_4$, HCl, or $HNO_3$ at a concentration of 0.1 to 5% (w/v) or with a high concentration (0.5 to 2.0 mol/L) NaOH or KOH solution. Preferably, the acidic or alkaline treatment is carried out at about 80~350° C. for 5~120 min.

Turning to pyrolysis, lignin can be degraded at as high as 350~650° C. using a high pressure reactor. The efficiency of pyrolysis can be increased in the presence of a catalyst such as nitrobenzene, $KMnO_4$, $H_2O_2$, zeolite, etc. In addition, the degradation of lignin can be accomplished using other physicochemical methods such as hydrogenolysis and hydrolysis under supercritical conditions.

The degradation of lignin is preferably carried out at an oxygen pressure of 2-20 bar. In addition, the degradation processes are preferably completed within 200 min, but the duration may be adjusted appropriately.

The lignin breakdown products include a mixture of aromatic monomers including aromatic aldehydes, such as vanillin, syringaldehyde, p-hydroxybenzaldehyde, and aromatic carboxylic acid such as vanillic acid, syringic acid, p-hydroxybenzoic acid, etc., and contain compounds of Chemical Formulae 1 and/or 2.

In accordance with an aspect thereof, the present invention addresses a process of biologically producing an aromatic carboxylic acid represented by Chemical Formula 1, or a derivative thereof; comprising:

degrading lignin to give a lignin breakdown product including an aromatic carboxylic acid having a p-hydroxy group of Chemical Formula 2; and contacting the lignin breakdown product with a biocatalyst having an activity to remove a p-hydroxy group from the aromatic carboxylic acid of Chemical Formula 2.

When X and Y in Chemical Formula 2 are not simultaneously hydrogen, the process may further comprise applying biocatalyst having an activity to remove at least one substituent selected from the group consisting of hydroxy and C1-C4 alkoxy at either or both positions 3 and 5, prior to, simultaneously with, or after the contact with the biocatalyst having an activity to remove a p-hydroxy group.

In addition, when the lignin breakdown product contains an aromatic aldehyde compound of Chemical Formula 3, such as vanillin, syringaldehyde, etc., the process may further comprise converting the lignin breakdown product into the compound of Chemical Formula 2 by oxidation, prior to or simultaneously with the contact of the lignin breakdown product including the compound of Chemical Formula 2 with the biocatalyst having an activity to remove p-hydroxy from the compound of Chemical Formula 2.

[Chemical Formula 3]

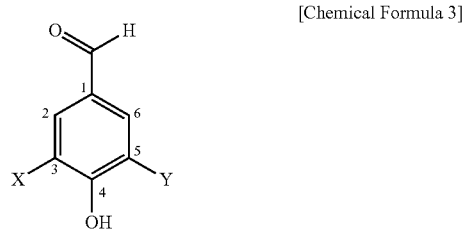

For example, conversion from the aromatic aldehyde of Chemical Formula 3 to the aromatic carboxylic acid of Chemical Formula 2 may be via chemical or biological reaction.

For chemical conversion, a silver oxide method or a caustic fusion method may be utilized. First, aromatic monomers with an aldehyde functional group are reacted with 1 M NaOH at 55~60° C. for about 10 min in the presence of 1 M $Ag_2O$, followed by neutralization with the equal amount of 1 M HCl with agitation to afford the aromatic carboxylic acid as a precipitate.

The biodegradation is characterized by the use of a biocatalyst such as an enzyme, a whole microbial cell, a microbial cell lysate, or a cell extract. The enzyme useful in the present invention may be exemplified by aldehyde dehydrogenase (EC 1.2.1.3, EC 1.2.1.4, EC 1.2.1.5), vanillin dehydrogenase (EC 1.2.1.67) and other enzymes functionally corresponding thereto. Non-limiting examples of these enzymes include GenBank ID CAD60262.1, ABK09332.1, Uniprot ID P47771, and P54114. Reactions may be performed in the presence of a pure enzyme as well as microbial whole cells expressing the enzyme or functionally identical enzymes, such as *Saccharomyces cerevisiae, Bacillus subtilis, Escherichia coli, Pseudomonas fluorescens, Pseudomonas putida, Serratia marcescens, Sphingomonas paucimobilis, Streptomyces viridosporus, Desulfovibrio vulgaris*, or *Burkholderia cepacia*, or a lysate or extract thereof. The aldehyde dehydrogenase may have an amino acid sequence (ALD4) as set forth in SEQ ID NO: 6.

Oxidative decarboxylation of the aromatic carboxylic acid produced by removal of p-hydroxy according to the present invention, particularly, benzoic acid or a derivative thereof; is an important route in the manufacture of bio-derived phenol. Alternatively, when a carboxylic acid is introduced thereto at para-position, the aromatic carboxylic acid can be converted into terephthalic acid or a derivative thereof which is in turn polycondensed with diols to manufacture polyethylene terephthalate (hereinafter referred to as "PET"). Superior in strength, hygroscopicity, and wrinkle recovery, PET is widely used in synthetic fibers. In addition, PET is widely used in a variety of packaging products due to its transparency, mechanical properties, and gas barrier properties. For example, foods, soft drinks, alcoholic beverages, detergents, cosmetics, drugs, and edible oils are packed in PET bottles.

A better understanding of the present invention may be obtained through the following examples which are set forth to illustrate the present invention, but are not to be construed as limiting the present invention.

<Analysis of Aromatic Monomers>

For use in the quantitative analysis of lignin-derived aromatic monomers, standard solutions of enzymatic reaction intermediates including p-hydroxybenzoic acid, benzoic acid and terephthalic acid were prepared, and analyzed using Waters e2695 HPLC equipped with a Waters 2489 UV/VIS (254 nm, 280 nm) detector (FIG. 1). For analysis, an)(Bridge C18 column (4.6×150 mm, 5 μm) was employed, and maintained at 35° C., with a mobile phase moved at 1 mL/min. The mobile phase was a mixture of A) a 5% acetonitrile solution containing 0.1% formic acid, and B) a 50% acetonitrile solution containing 0.1% formic acid, and was applied in the following gradient elution manner: 1.5 min (0% B), 9.5 min (90% B), 16.5 min (40% B), 21.5 min (24% B), and 24.5 min (0% B). Prior to subsequent analysis, the column was pre-equilibrated for 6 min.

The generation of benzoic acid was monitored using HPLC and ESI-MS/MS (Waters TQD). This HPLC was conducted in the same condition as in the above HPLC. The condition for mass spectrometry was optimized with a p-hydroxybenzoic acid standard solution. Mass spectra were obtained in the positive mode and the optimal condition for the spectrometry was set forth as follows: Capillary voltage: 3 kV, Cone voltage: 25 V, Source temperature: 120° C., Desolvation temperature: 300° C., Desolvation gas flow: 600 L/hr (N2), and Cone gas flow: 60 L/hr (N2). On the HPLC-ESI-MS/MS spectra, a peak for benzoic acid was detected, in comparison with the standard solution, in the scan mode (50~200, m/z) as molecular ions and specific fragment ions were generated at a given collision energy.

Example 1

Production of Benzoic Acid by Dehydroxylation

<Step 1> Construction of Recombinant Expression Vector Carrying Prephenate Hydro-Lyase (PHA2) Gene and Preparation of Transformed Microorganism To produce prephenate hydro-lyase (PHA2), a PHA2 gene from *S. cerevisiae* was cloned. First, genomic DNA was isolated from *S. cerevisiae* ATCC 204508. On the basis of a nucleotide sequence (GenBank Accession Number; CAA86380.1) coding for a PHA2 gene, the following primers were designed:

```
Forward primer 1 (SEQ ID NO: 7):
5'-AAACATATG AAAATAAAAATTTTAGTAGA-3'

Reverse primer 1 (SEQ ID NO: 8):
5'-AAACTCGAG TTTGTGATAATATCTCTCAT-3'
```

The nucleotide sequence of PHA2 gene was amplified by PCR using the primers, with the genomic DNA of *S. cerevisiae* ATCC 204508 serving as a template.

A total volume of 50 µl of a PCR composition contained 100 ng of the template, 10 pmol of each primer, 2.5 mM dNTPs, a 1×PCR buffer, and a 2.5 U Taq polymerase. PCR started with pre-denaturation at 94° C. for 5 min, and was performed with 30 cycles of denaturation at 95° C. for 1 min; annealing at 54° C. for 30 sec; and elongation at 72° C. for 2 min, followed by post-polymerization at 72° C. for 5 min for final elongation.

The PCR product thus obtained was digested with NdeI/XhoI restriction enzymes, and inserted in the presence of T4 DNA ligase into the plasmid vector pET28a (Novagen) which was previously cut with the same enzymes, to construct a recombinant pET28a/PHA2 vector. PCR and cloning results were monitored by 1.2% agarose electrophoresis.

The recombinant expression vector was typically transformed into *E. coli* BL21 (DE3), and the transformant was cryo-preserved in 15% glycerol until use for enzyme expression.

<Step 2> Production of Prephenate Hydro-Lyase

To produce prephenate hydro-lyase in a large amount, the cryo-preserved recombinant *E. coli* was inoculated into 5 mL of LB broth in a test tube, and seed cultured at 37° C. with agitation to an absorbance of 2.5 at 600 nm. Then, the seed culture was added to 100 mL of LB broth in a 300 mL flask and cultured. When absorbance at 600 nm reached 0.6, 1 mM IPTG was added to induce the expression of the enzyme. In this regard, the cells were cultured at 30° C. with agitation at 250 rpm, and further incubated for 10 hrs after IPTG addition.

Then, the transformed cell culture was centrifuged at 4,000×g and 4° C. for 30 min, washed twice with a PBS buffer, mixed with a 50 mM Tris-HCl buffer (pH 7.5) before ultrasonic disruption. The cell lysate was again centrifuged at 13,000×g and 4° C. for 20 min, and the supernatant was withdrawn and subjected to Ni-NTA His-Tag chromatography to separate the enzyme. The bound enzyme was eluted with a 50 mM Tris-HCl buffer (pH 7.5) using a centrifugal separation filter (10 kDa). After concentration, the eluate was quantitatively analyzed using a protein assay (Bradford). Finally, the enzyme was obtained at a concentration of 5 mg/mL, and used in a enzymatic reaction with p-hydroxybenzoic acid as a substrate. Proteins were analyzed on 12% polyacrylamide gel by electrophoresis.

<Step 3> Production of Benzoic Acid

To 0.5 mL of a mixture containing 10 mM p-hydroxybenzoic acid (Sigma), 1 mM EDTA, 20 mM 2-mercaptoethanol, 50 µL of the 5 mg/L prephenate hydro-lyase purified in step 2 was added. After reaction for 5 hrs in a 37° C. incubator, three volumes of 1 N sodium hydroxide were added to the reaction mixture which was then filtered through a syringe filter (0.22 µm) to remove impurities. Concentrations of p-hydroxybenzoic acid and benzoic acid in the resulting sample were monitored using HPLC, and the results are given in Table 3.

TABLE 3

| | Before enzyme reaction (mM) | After enzyme reaction (mM) |
|---|---|---|
| p-hydroxybenzoic acid | 9.98 | 2.46 |
| benzoic acid | 0.00 | 6.12 |

Figure 2A:
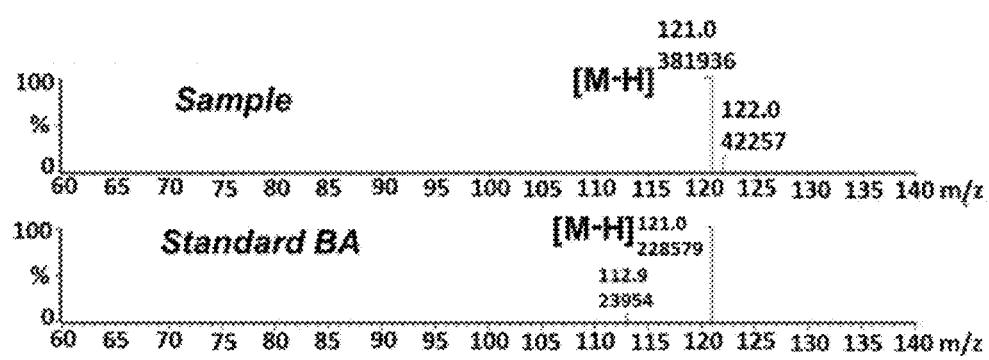
FIGS. 2A and 2B shows mass spectra of benzoic acid, as measured (A) in the MS spectrum scan mode (60-200 m/z) and (B) in the MS/MS spectrum daughter scan mode (121→60-140 m/z).
Figure 2B:
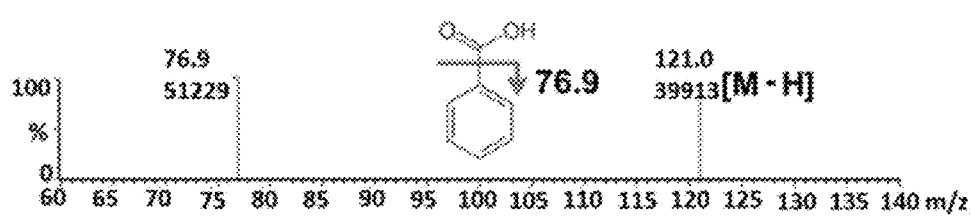

As shown in Table 3, p-hydroxybenzoic acid was converted into benzoic acid by prephenate hydro-lyase. The production of benzoic acid was confirmed by the mass spectroscopic analysis as shown in FIGS. 2A and 2B.

Example 2

Production of Aminodeoxychorismate Lyase

<Step 1> Construction of Recombinant Expression Vector Carrying Aminodeoxychorismate Lyase Gene and Preparation of Transformed Microorganism To produce aminodeoxychorismate lyase (ADC lyase), an ADC lyase gene from *S. cerevisiae* was cloned. First, genomic DNA was isolated from *S. cerevisiae* KCCM 50712. On the basis of a nucleotide sequence (GenBank Accession Number; DAA10190.1) coding for the ADC lyase of *S. cerevisiae* KCCM 50712, the following primers were designed:

```
Forward primer 2 (SEQ ID NO: 9):
5'-AAACATATG TCACTAATGGACAATTGGAA-3

Reverse primer 2 (SEQ ID NO: 10):
5'-AAACTCGAG ATATTTTGTCTTCACTGTTC-3'
```

The nucleotide sequence of ADC lyase gene was amplified by PCR using the primers, with the genomic DNA of *S. cerevisiae* KCCM 50712 serving as a template.

A total volume of 50 µl of a PCR composition contained 100 ng of the template, 10 pmol of each primer, 2.5 mM dNTPs, a 1×PCR buffer, and a 2.5 U Taq polymerase. PCR started with pre-denaturation at 94° C. for 5 min, and was performed with 30 cycles of denaturation at 94° C. for 1 min; annealing at 55° C. for 30 sec; and elongation at 72° C. for 3 min, followed by post-polymerization at 72° C. for 5 min for final elongation.

The PCR product thus obtained was digested with NdeI/XhoI restriction enzymes, and inserted in the presence of T4 DNA ligase into the plasmid vector pET28a (Novagen) which was previously cut with the same enzymes, to construct a recombinant pET28a/ADCL vector. PCR and cloning results were monitored by 1.2% agarose electrophoresis.

The recombinant expression vector was typically transformed into *E. coli* BL21 (DE3), and the transformant was cryo-preserved in 15% glycerol until use for enzyme expression.

<Step 2> Production of ADC Lyase

To produce ADC lyase in a large amount, the cryo-preserved recombinant *E. coli* was inoculated into 5 mL of LB broth in a test tube, and seed cultured at 37° C. with agitation to an absorbance of 2.5 at 600 nm. Then, the seed culture was added to 100 mL of LB broth in a 300 mL flask and cultured. When absorbance at 600 nm reached 0.6, 0.5 mM IPTG was added to induce the expression of the enzyme. In this regard, the cells were cultured at 33° C. with agitation at 250 rpm, and further incubated for 6 hrs after IPTG addition.

Then, the transformed cell culture was centrifuged at 4,000×g and 4° C. for 20 min, washed twice with a PBS buffer, mixed with a 50 mM Tris-HCl buffer (pH 7.5) before ultrasonic disruption. The cell lysate was again centrifuged at 13,000×g and 4° C. for 20 min, and the supernatant was withdrawn and subjected to Ni-NTA His-Tag chromatography to purify the enzyme. The bound enzyme was eluted with a 50 mM Tris-HCl buffer (pH 7.5) using a centrifugal separation filter (10 kDa). After concentration, the eluate was quantitatively analyzed using a protein assay (Bradford). Finally, the enzyme was obtained at a concentration of 5 mg/mL, and used in enzymatic reaction.

Example 3

Production of Benzoic Acid by Enzymatic Reaction Using Lignin Degradation Product as Substrate Lignin was degraded using a laboratory high-pressure reactor (450 mL, Parr 4562). A reactant with a lignin content of 5.0% (w/v) was prepared by adding 10.0 g of graft lignin to 200 mL of 1 M NaOH. The reactant was further mixed with 10 g of the catalyst $KMnO_4$, loaded to a stainless steel high-pressure reactor with an internal volume of 450 mL, sealed, and stirred at a speed of 500 rpm. After the reactor was filled with oxygen gas at a pressure of about 5 bar for 2 min via a sampling line communicating with the interior thereof, it was heated. When the internal temperature of the reactor reached 140° C., the reaction was continued for 60 min. The reaction temperature was adjusted by a PID controller through a cooling water tube. At 60 min of the reaction, a sample was withdrawn via a sampling line, and then, the reaction was terminated.

Two mL of the sample containing alkaline breakdown products of lignin was 3-fold diluted in 4 mL of distilled water, followed by removal of lignin by filtration (10 kDa MWCO). To 1 mL of the lignin-free sample were added 9 volumes of methanol, and lignin breakdown products were purified by filtration through a syringe filter (0.22 µm).

The lignin breakdown products obtained above were enzymatically converted into p-hydroxybenzoic acid. In this regard, a solution of the lignin breakdown products was adjusted to pH 8.0 using a small amount of 10 M HCl, and filtered through a 10 kDa MWCO filter. The filtrate was used as a substrate in reaction with a mixture of 50 µL of 5 mg/mL aminodeoxychorismate lyase (ADC lyase), obtained in Example 2, and 50 µL of 5 mg/ml aldehyde dehydrogenase (Sigma A6338, ALD4) for 3 hrs in a 37° C. incubator. Of the reaction mixture, 50 µL was withdrawn and used for analysis while the remainder was used as a substrate for a subsequent enzyme reaction. For p-hydroxybenzoic acid analysis, the sample was extracted with 9 volumes of methanol (450 µL), and filtered through a syringe filter (0.22 µm). The resulting sample was analyzed for p-hydroxybenzoic acid by HPLC (Table 4).

The enzyme reaction mixture containing p-hydroxybenzoic acid was treated with the prephenate hydro-lyase (dehydroxylase) of Example 1 to generate benzoic acid. Briefly, the prephenate hydro-lyase of Example 1 was added at a final concentration of 500 µg/mL to 400 µL of the remainder enzyme reaction mixture which was then mixed with sodium bicarbonate at a final concentration of 100 mM, followed by reaction for 10 hrs in a 37° C. anaerobic chamber. After completion of the reaction, the sample was filtered through a syringe filter (0.22 µm) to remove impurities. Analysis results of the sample are summarized in Table 4, below.

TABLE 4

| Compound | Lignin degradation Product (mM) | Product obtained after treatment with aldehyde dehydroganase and ADC lyase (mM) | Product obtained after treatment with dehydroxylase (mM) |
| --- | --- | --- | --- |
| p-Hydroxybenzoic acid | 0.21 | 4.53 | 1.52 |
| p-Hydroxybenzaldehyde | 0.91 | 0.18 | 0.00 |

TABLE 4-continued

| Compound | Lignin degradation Product (mM) | Product obtained after treatment with aldehyde dehydroganase and ADC lyase (mM) | Product obtained after treatment with dehydroxylase (mM) |
| --- | --- | --- | --- |
| Vanillic acid | 2.40 | 1.95 | 1.25 |
| Vanillin | 5.82 | 2.98 | 1.32 |
| Syringic acid | 0.50 | 0.12 | 0.00 |
| Syrinaldehyde | 0.21 | 0.00 | 0.00 |
| Benzoic acid | 0.00 | 0.00 | 1.86 |

As can be seen in the Table 4, lignin breakdown products contain p-hydroxybenzoic acid, p-hydroxybenzaldehyde, vanillic acid, vanillin, syringic acid and syringaldehyde. Vanillic acid and syringic acid were demethoxylated to p-hydroxybenzoic acid by ADC lyase. Vanillin, p-hydroxybenzaldehyde and syringaldehyde were first oxidized by aldehyde dehydrogenase to vanillic acid, p-hydroxybenzoic acid and syringic acid, respectively. The resulting vanillic acid and syringic acid were further converted to p-hydroxybenzoic acid by ADC lyase. Subsequently, the p-hydroxy group of p-hydroxybenzoic acid was removed in the presence of dehydroxylase to give 1.86 mM benzoic acid.

Example 4

Production of Terephthalic Acid

<Step 1> Construction of Recombinant Expression Vector Carrying 4-Hydroxybenzoic Acid Decarboxylase Gene and Preparation of Transformed Microorganism To produce 4-hydroxybenzoic acid, bsdB, bsdC and bsdD genes from *Bacillus subtilis* (strain 168) were cloned. Decarboxylase was known to catalyze decarboxylation reversibly according to reaction condition and substrate (Can. J. Microbiol. 54: 75-81 (2008)). In the present invention, the enzyme was used to introduce a carboxyl group to the position 4' of benzoic acid. Genomic DNA was isolated from *B. subtilis* ATCC 6051. On the basis of nucleotide sequences coding for 4-hydroxybenzoic acid decarboxylase genes (GenBank Accession Number; bsdB:BAA08996.1., bsdC: BAA08997.1., bsdD: CAX52546.1.), the following primers were designed. A 4-hydroxybenzoic acid decarboxylase is a complex composed of three enzymes for which the genes bsdB, bsdC, and bsdD code (SEQ ID NOS: 13, 15, and 17, respectively). Because these genes are polycistronic, they could be cloned with the following primers.

```
Forward primer 3 (SEQ ID NO: 11):
5'-AAACATATG AAAGCAGAATTCAAGCGTAA-3'

Reverse primer 3 (SEQ ID NO: 12):
5'-AAACTCGAG AGCCTTTCGTTCCGGCACCG-3'
```

The 4-hydroxybenzoic acid decarboxylase gene was amplified by PCR using the primers, with the genomic DNA of *B. subtilis* ATCC 6051 serving as a template.

A total volume of 50 µl of a PCR composition contained 100 ng of the template, 10 pmol of each primer, 2.5 mM dNTPs, a 1×PCR buffer, and a 2.5 U Taq polymerase. PCR started with pre-denaturation at 95° C. for 5 min, and was performed with 30 cycles of denaturation at 95° C. for 1 min; annealing at 54° C. for 30 sec; and elongation at 72° C. for 3 min, followed by post-polymerization at 72° C. for 5 min for final elongation.

The PCR product thus obtained was digested with NdeI/XhoI restriction enzymes, and inserted in the presence of T4 DNA ligase into the plasmid vector pET28a (Novagen) which was previously cut with the same enzymes, to construct a recombinant pET28a/PAD vector. PCR and cloning results were monitored by 1.2% agarose electrophoresis.

The recombinant expression vector was typically transformed into *E. coli* BL21 (DE3), and the transformant was cryo-preserved in 15% glycerol until use for enzyme expression.

<Step 2> Production of Carboxylase

To produce 4-hydroxybenzoic acid decarboxylase in a large amount, the cryo-preserved recombinant *E. coli* (DE3) was inoculated into 5 mL of LB broth in a test tube, and seed cultured at 37° C. with agitation to an absorbance of 2.5 at 600 nm. Then, the seed culture was added to 100 mL of LB broth in a 300 mL flask and cultured. When absorbance at 600 nm reached 0.6, 1 mM IPTG was added to induce the expression of the enzyme. In this regard, the cells were cultured at 30° C. with agitation at 250 rpm, and further incubated for 10 hrs after IPTG addition.

Then, the transformed cell culture was centrifuged at 4,000×g and 4° C. for 30 min, washed twice with a PBS buffer, mixed with a 50 mM Tris-HCl buffer (pH 7.5) before ultrasonic disruption. The cell lysate was again centrifuged at 13,000×g and 4° C. for 20 min, and the supernatant was withdrawn and subjected to Ni-NTA His-Tag chromatography to separate the enzyme. The bound enzyme was eluted with a 50 mM Tris-HCl buffer (pH 8.0) using a centrifugal separation filter (10 kDa). After concentration, the eluate was quantitatively analyzed using a protein assay (Bradford). Finally, the enzyme was obtained at a concentration of 5 mg/mL, and used in enzymatic reaction with benzoic acid as a substrate.

<Step 3> Production of Terephthalic Acid

To the enzyme reaction mixture containing p-hydroxybenzoic acid obtained in Example 3, each dehydroxylase of Example 1 and carboxylase purified in step 2 were added to a final concentration of 500 µg/mL. Then, the enzyme solution was mixed with sodium bicarbonate at a final concentration of 100 mM, followed by reaction for 10 hrs in a 37° C. anaerobic chamber. After completion of the reaction, the reaction mixture was mixed with three volumes of 1 N sodium hydroxide, and filtered through a syringe filter (0.22 µm) to remove impurities. Analysis results of the sample are summarized in Table 5, below.

TABLE 5

| Compound | Product obtained after Treatment with Dehydroxylase and Carboxylase (mM) |
|---|---|
| p-Hydroxybenzoic acid | 1.35 |
| p-Hydroxybenzaldehyde | 0.00 |
| Vanillic acid | 1.24 |
| Vanillin | 1.32 |
| Syringic acid | 0.00 |
| Syrinaldehyde | 0.00 |
| Benzoic acid | 0.52 |
| Terephthalic acid | 1.16 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of biologically producing an aromatic carboxylic acid of Chemical Formula 1, the method comprising contacting a substrate containing an aromatic carboxylic acid having a para-hydroxy group represented by Chemical Formula 2 with a biocatalyst that removes the para-hydroxy group:

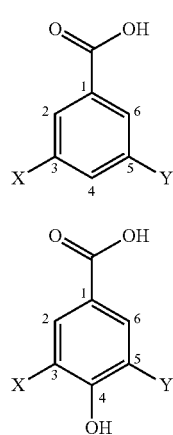

[Chemical Formula 1]

[Chemical Formula 2]

wherein, X and Y are independently hydrogen, hydroxy, or C1-C4 alkoxy, and wherein the biocatalyst that removes the para-hydroxy group comprises at least one enzyme selected from the group consisting of 3 dehydroquinate hydro-lyase (EC 4.2.1.10), aldos-2-ulose dehydratase (EC 4.2.1.110), o-succinylbenzoate synthase (EC 4.2.1.113), 3-dehydroshikimate hydro-lyase (EC 4.2.1.118), prephenate hydro-lyase (EC 4.2.1.51), arogenate dehydratase (EC 4.2.1.91), scytalone 7,8-hydro-lyase (EC 4.2.1.94), and 16α-hydroxyprogesterone hydro-lyase (EC 4.2.1.98).

2. The method of claim 1, wherein X and Y are not simultaneously hydrogen in Chemical Formula 2, and the method further comprises contacting the substrate with a biocatalyst that removes a substituent selected from the group consisting of hydroxy and C1-C4 alkoxy located at position 3, position 5, or both of positions 3 and 5 of the benzene ring, before, simultaneously with, or after contacting with the biocatalyst that removes the para-hydroxy group, wherein the biocatalyst that removes at least one substituent selected from the group consisting of para-hydroxy and C1-C4 alkoxy is an enzyme selected from the group consisting of anthranilate synthase (EC 4.1.3.27), aminodeoxychorismate lyase (EC 4.1.3.38), and chorismate lyase (EC 4.1.3.40).

3. The method of claim 1, wherein the substrate also comprises an aromatic aldehyde of Chemical Formula 3, and the method further comprises converting the aromatic aldehyde to the aromatic carboxylic acid of Chemical Formula 2 by chemical oxidation or biocatalytic oxidation prior to contacting with the biocatalyst that removes the para-hydroxy group from the aromatic carboxylic acid of Chemical Formula 2:

[Chemical Formula 2]

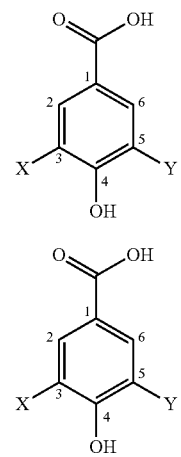

[Chemical Formula 3]

wherein, X and Y are independently hydrogen, hydroxy, or $C_1$-$C_4$ alkoxy.

4. The method of claim 3, wherein X and Y are not simultaneously hydrogen in Chemical Formula 3, and the method further comprises contacting the substrate with a biocatalyst that removes a substituent selected from the group consisting of hydroxy and $C_1$-$C_4$ alkoxy located at position 3, position 5, or both of positions 3 and 5 of the benzene ring before, simultaneously with, or after the oxidation of the aromatic aldehyde of Chemical Formula 3.

5. The method of claim 1, wherein contacting the substrate with the biocatalyst comprises contacting the substrate with the at least one enzyme, a microorganism containing the at least one enzyme, a lysate of the microorganism, or an extract from the lysate of the microorganism, or culturing the microorganism in a medium containing the substrate.

6. The method of claim 4, wherein the biocatalyst that removes at least one substituent selected from the group consisting of para-hydroxy and $C_1$-$C_4$ alkoxy is an enzyme selected from the group consisting of anthranilate synthase (EC 4.1.3.27), aminodeoxychorismate lyase (EC 4.1.3.38), and chorismate lyase (EC 4.1.3.40), a microorganism that produces at least one of the foregoing enzymes; a lysate of a microorganism containing at least one of the foregoing enzymes; or an extract from the lysate of the microorganism containing at least one of the foregoing enzymes.

7. The method of claim 3, wherein the compound of Chemical Formulae 2 or 3 is derived from lignin.

8. The method of claim 7, wherein the substrate containing an aromatic carboxylic acid having a para-hydroxy group of Chemical Formula 2, is obtained by:
   degrading lignin to give a lignin degradation product comprising the aromatic carboxylic acid having a para-hydroxy group of Chemical Formula 2.

9. The method of claim 8, wherein X and Y are not simultaneously hydrogen in Chemical Formula 2, and the method further comprises contacting the substrate with a biocatalyst that removes a substituent selected from the group consisting of hydroxy and $C_1$-$C_4$ alkoxy located at positions 3, position 5, or both of positions 3 and 5 of the benzene ring, before, simultaneously with, or after contacting with the biocatalyst that removes the para-hydroxy group.

10. The method of claim 8, further comprising converting an aromatic aldehyde represented by the following Chemical Formula 3 to the aromatic carboxylic acid of Chemical Formula 2 by chemical oxidation or biocatalytic oxidation, before or simultaneously with contacting with the biocatalyst that removes the para-hydroxy group.

11. The method of claim 8, wherein the degradation of lignin involves at least one selected from the group consisting of pyrolysis, gasification, hydrogenolysis, acidolysis, alkaline lysis, chemical oxidation, hydrolysis under supercritical conditions, and enzymolysis.

12. The method of claim 2, wherein contacting the substrate with the biocatalyst comprises contacting the substrate with the at least one enzyme, a microorganism containing the at least one enzyme, a lysate of the microorganism, or an extract from the lysate of the microorganism, or culturing the microorganism in a medium containing the substrate.

* * * * *

SEQUENCE LISTING

<160> NUMBER OF SEQ ID NOS: 18

<210> SEQ ID NO 1
<211> LENGTH: 1107
<212> TYPE: DNA
<213> ORGANISM: Saccharomyces cerevisiae

<400> SEQUENCE: 1

```
atgaaaataa aaatttttagt agatgaatat aatacgcaga aagaacaggc taaaaaagta      60
cgaaaagcaa cttcattata tttccgcatt catccttcaa ttatggccag caagactttg     120
agggttcttt ttctgggtcc caaaggtacg tattcccatc aagctgcatt acaacaattt     180
caatcaacat ctgatgttga gtacctccca gcagcctcta tcccccaatg ttttaaccaa     240
ttggagaacg acactagtat agattattca gtggtaccgt tggaaaattc caccaatgga     300
caagtagttt tttcctatga tctcttgcgt gataggatga tcaaaaaagc cctatcctta     360
cctgctccag cagatactaa tagaattaca ccagatatag aagttatagc ggagcaatat     420
gtacccatta cccattgtct aatcagccca atccaactac caaatggtat tgcatccctt     480
ggaaattttg aagaagtcat aatacactca catccgcaag tatggggcca ggttgaatgt     540
tacttaaggt ccatggcaga aaaatttccg caggtcacct ttataagatt ggattgttct     600
tccacatctg aatcagtgaa ccaatgcatt cggtcatcaa cggccgattg cgacaacatt     660
ctgcatttag ccattgctag tgaaacagct gcccaattgc ataaggcgta catcattgaa     720
cattcgataa atgataagct aggaaataca acaagatttt tagtattgaa gagaagggag     780
aacgcaggcg acaatgaagt agaagacact ggattactac gggttaacct actcacccttt     840
```

```
actactcgtc aagatgaccc tggttctttg gtagatgttt tgaacatact aaaaatccat      900
tcactcaaca tgtgttctat aaactctaga ccattccatt tggacgaaca tgatagaaac      960
tggcgatatt tatttttcat tgaatattac accgagaaga ataccccaaa gaataaagaa     1020
aaattctatg aagatatcag cgacaaaagt aaacagtggt gcctgtgggg tacattcccc     1080
agaaatgaga gatattatca caaataa                                         1107
```

<210> SEQ ID NO 2
<211> LENGTH: 367
<212> TYPE: PRT
<213> ORGANISM: Saccharomyces cerevisiae

<400> SEQUENCE: 2

```
Met Lys Ile Lys Ile Leu Val Asp Glu Tyr Asn Thr Gln Lys Glu Gln
1               5                   10                  15

Ala Lys Lys Val Arg Lys Ala Thr Ser Leu Tyr Phe Arg Ile His Pro
            20                  25                  30

Ser Ile Met Ala Ser Lys Thr Leu Arg Val Leu Phe Leu Gly Pro Lys
        35                  40                  45

Gly Thr Tyr Ser His Gln Ala Ala Leu Gln Gln Phe Gln Ser Thr Ser
    50                  55                  60

Asp Val Glu Tyr Leu Pro Ala Ala Ser Ile Pro Gln Cys Phe Asn Gln
65                  70                  75                  80

Leu Glu Asn Asp Thr Ser Ile Asp Tyr Ser Val Val Pro Leu Glu Asn
                85                  90                  95

Ser Thr Asn Gly Gln Val Val Phe Ser Tyr Asp Leu Leu Arg Asp Arg
            100                 105                 110

Met Ile Lys Lys Ala Leu Ser Leu Pro Ala Pro Ala Asp Thr Asn Arg
        115                 120                 125

Ile Thr Pro Asp Ile Glu Val Ile Ala Glu Gln Tyr Val Pro Ile Thr
    130                 135                 140

His Cys Leu Ile Ser Pro Ile Gln Leu Pro Asn Gly Ile Ala Ser Leu
145                 150                 155                 160

Gly Asn Phe Glu Glu Val Ile Ile His Ser His Pro Gln Val Trp Gly
                165                 170                 175

Gln Val Glu Cys Tyr Leu Arg Ser Met Ala Glu Lys Phe Pro Gln Val
            180                 185                 190

Thr Phe Ile Arg Leu Asp Cys Ser Ser Thr Ser Glu Ser Val Asn Gln
        195                 200                 205

Cys Ile Arg Ser Ser Thr Ala Asp Cys Asp Asn Ile Leu His Leu Ala
    210                 215                 220

Ile Ala Ser Glu Thr Ala Ala Gln Leu His Lys Ala Tyr Ile Ile Glu
225                 230                 235                 240

His Ser Ile Asn Asp Lys Leu Gly Asn Thr Thr Arg Phe Leu Val Leu
                245                 250                 255

Lys Arg Arg Glu Asn Ala Gly Asp Asn Glu Val Glu Asp Thr Gly Leu
            260                 265                 270

Leu Arg Val Asn Leu Leu Thr Phe Thr Thr Arg Gln Asp Asp Pro Gly
        275                 280                 285

Ser Leu Val Asp Val Leu Asn Ile Leu Lys Ile His Ser Leu Asn Met
    290                 295                 300

Cys Ser Ile Asn Ser Arg Pro Phe His Leu Asp Glu His Asp Arg Asn
305                 310                 315                 320
```

Trp Arg Tyr Leu Phe Phe Ile Glu Tyr Tyr Thr Glu Lys Asn Thr Pro
            325                 330                 335

Lys Asn Lys Glu Lys Phe Tyr Glu Asp Ile Ser Asp Lys Ser Lys Gln
            340                 345                 350

Trp Cys Leu Trp Gly Thr Phe Pro Arg Asn Glu Arg Tyr Tyr His
            355                 360                 365

<210> SEQ ID NO 3
<211> LENGTH: 1125
<212> TYPE: DNA
<213> ORGANISM: Saccharomyces cerevisiae

<400> SEQUENCE: 3

```
atgtcactaa tggacaattg gaagactgat atggaaagtt acgatgaagg aggcctagtt      60
gctaatccga acttcgaggt tctggccact ttcaggtacg accctggttt tgcacgccag     120
tcagcgtcaa agaaagagat cttttgaaact ccagaccctc gattaggttt gagagacgaa    180
gatattaggc agcagataat taatgaggat tactcaagtt atttacgagt aagggaggtt     240
aattccggcg gtgaccttct cgaaaatatt cagcatcctg atgcttggaa gcatgattgc     300
aagaccattg tgtgccagcg tgtagaagat atgctacaag tcatttatga acgatttttt     360
ttattagatg aacaatacca agaataaga atagcattat catactttaa aattgacttc      420
agcacgtctc tgaatgattt attgaagtta ttggttgaaa acttgattaa ttgtaaagaa     480
ggaaattcag agtatcacga aaaaattcaa aaaatgatca acgaaaggca atgctataaa     540
atgcgggtac ttgtctctaa gacaggagat atacgaattg aggcaattcc aatgcctatg     600
gagcctatcc taaaattaac aaccgattat gacagtgttt ccacatactt catcaaaacg     660
atgctcaatg gatttttaat tgatagcaca ataaattggg atgttgttgt ttcatctgaa     720
ccattgaacg catcagcttt caccagtttt aaaaccactt caagagatca ttacgctagg    780
gcgagagttc gcatgcaaac tgctataaat aacttaagag gttcagaacc tacttcttct     840
gtctcgcaat gcgaaatttt attttccaac aaatctggcc tgctgatgga aggttcaata    900
acaaacgtgg ctgtaattca aaaagatcct aacggttcta aaagtatgt gacaccaaga     960
ttagcaactg gatgtttgtg cggaacaatg cgtcattatt tattgcggct cggccttatt    1020
gaagagggag atatagatat aggaagcctt accgttggca acgaagtttt gcttttcaat    1080
ggcgtcatgg gatgcataaa gggaacagtg aagacaaaat attga                    1125
```

<210> SEQ ID NO 4
<211> LENGTH: 374
<212> TYPE: PRT
<213> ORGANISM: Saccharomyces cerevisiae

<400> SEQUENCE: 4

Met Ser Leu Met Asp Asn Trp Lys Thr Asp Met Glu Ser Tyr Asp Glu
1               5                   10                  15

Gly Gly Leu Val Ala Asn Pro Asn Phe Glu Val Leu Ala Thr Phe Arg
            20                  25                  30

Tyr Asp Pro Gly Phe Ala Arg Gln Ser Ala Ser Lys Lys Glu Ile Phe
        35                  40                  45

Glu Thr Pro Asp Pro Arg Leu Gly Leu Arg Asp Glu Asp Ile Arg Gln
    50                  55                  60

Gln Ile Ile Asn Glu Asp Tyr Ser Ser Tyr Leu Arg Val Arg Glu Val
65                  70                  75                  80

Asn Ser Gly Gly Asp Leu Leu Glu Asn Ile Gln His Pro Asp Ala Trp 85                  90                  95
Lys His Asp Cys Lys Thr Ile Val Cys Gln Arg Val Glu Asp Met Leu
            100                 105                 110

Gln Val Ile Tyr Glu Arg Phe Phe Leu Leu Asp Glu Gln Tyr Gln Arg
        115                 120                 125

Ile Arg Ile Ala Leu Ser Tyr Phe Lys Ile Asp Phe Ser Thr Ser Leu
    130                 135                 140

Asn Asp Leu Leu Lys Leu Val Glu Asn Leu Ile Asn Cys Lys Glu
145                 150                 155                 160

Gly Asn Ser Glu Tyr His Glu Lys Ile Gln Lys Met Ile Asn Glu Arg
                165                 170                 175

Gln Cys Tyr Lys Met Arg Val Leu Val Ser Lys Thr Gly Asp Ile Arg
            180                 185                 190

Ile Glu Ala Ile Pro Met Pro Met Glu Pro Ile Leu Lys Leu Thr Thr
        195                 200                 205

Asp Tyr Asp Ser Val Ser Thr Tyr Phe Ile Lys Thr Met Leu Asn Gly
    210                 215                 220

Phe Leu Ile Asp Ser Thr Ile Asn Trp Asp Val Val Ser Ser Glu
225                 230                 235                 240

Pro Leu Asn Ala Ser Ala Phe Thr Ser Phe Lys Thr Thr Ser Arg Asp
                245                 250                 255

His Tyr Ala Arg Ala Arg Val Arg Met Gln Thr Ala Ile Asn Asn Leu
            260                 265                 270

Arg Gly Ser Glu Pro Thr Ser Ser Val Ser Gln Cys Glu Ile Leu Phe
        275                 280                 285

Ser Asn Lys Ser Gly Leu Leu Met Glu Gly Ser Ile Thr Asn Val Ala
    290                 295                 300

Val Ile Gln Lys Asp Pro Asn Gly Ser Lys Lys Tyr Val Thr Pro Arg
305                 310                 315                 320

Leu Ala Thr Gly Cys Leu Cys Gly Thr Met Arg His Tyr Leu Leu Arg
                325                 330                 335

Leu Gly Leu Ile Glu Glu Gly Asp Ile Asp Ile Gly Ser Leu Thr Val
            340                 345                 350

Gly Asn Glu Val Leu Leu Phe Asn Gly Val Met Gly Cys Ile Lys Gly
        355                 360                 365

Thr Val Lys Thr Lys Tyr
    370

<210> SEQ ID NO 5
<211> LENGTH: 1560
<212> TYPE: DNA
<213> ORGANISM: Saccharomyces cerevisiae

<400> SEQUENCE: 5
atgttcagta gatctacgct ctgcttaaag acgtctgcat cctccattgg gagacttcaa      60
ttgagatatt tctcacacct tcctatgaca gtgcctatca agctgcccaa tgggttggaa     120
tatgagcaac caacgggggtt gttcatcaac aacaagtttg ttccttctaa acagaacaag    180
accttcgaag tcattaaccc ttccacggaa gaagaaatat gtcatattta tgaaggtaga    240
gaggacgatg tggaagaggc cgtgcaggcc gccgaccgtg ccttctctaa tgggtcttgg    300
aacggtatcg accctattga caggggtaag gctttgtaca ggttagccga attaattgaa    360
caggacaagg atgtcattgc ttccatcgag actttggata cggtaaagc tatctcttcc    420 tcgagaggag atgttgattt agtcatcaac tatttgaaat cttctgctgg ctttgctgat    480

```
aaaattgatg gtagaatgat tgatactggt agaacccatt tttcttacac taagagacag    540
cctttgggtg tttgtgggca gattattcct tggaatttcc cactgttgat gtgggcctgg    600
aagattgccc ctgctttggt caccggtaac accgtcgtgt tgaagactgc cgaatccacc    660
ccattgtccg ctttgtatgt gtctaaatac atcccacagg cgggtattcc acctggtgtg    720
atcaacattg tatccgggtt tggtaagatt gtgggtgagg ccattacaaa ccatccaaaa    780
atcaaaaagg ttgccttcac agggtccacg gctacgggta gacacattta ccagtccgca    840
gccgcaggct tgaaaaaagt gactttggag ctgggtggta aatcaccaaa cattgtcttc    900
gcggacgccg agttgaaaaa agccgtgcaa acattatcc ttggtatcta ctacaattct    960
ggtgaggtct gttgtgcggg ttcaagggtg tatgttgaag aatctattta cgacaaattc   1020
attgaagagt tcaaagccgc ttctgaatcc atcaaggtgg cgacccatt cgatgaatct   1080 actttccaag gtgcacaaac ctctcaaatg caactaaaca aaatcttgaa atacgttgac   1140
attggtaaga atgaaggtgc tactttgatt accggtggtg aaagattagg tagcaagggt   1200
tacttcatta agccaactgt ctttggtgac gttaaggaag acatgagaat tgtcaaagag   1260
gaaatctttg gccctgttgt cactgtaacc aaattcaaat ctgccgacga agtcattaac   1320
atggcgaacg attctgaata cgggttggct gctggtattc acacctctaa tattaatacc   1380
gccttaaaag tggctgatag agttaatgcg ggtacggtct ggataaacac ttataacgat   1440
ttccaccacg cagttccttt cggtgggttc aatgcatctg gtttgggcag ggaaatgtct   1500
gttgatgctt tacaaaacta cttgcaagtt aaagcggtcc gtgccaaatt ggacgagtaa   1560
```

<210> SEQ ID NO 6
<211> LENGTH: 519
<212> TYPE: PRT
<213> ORGANISM: Saccharomyces cerevisiae

<400> SEQUENCE: 6

```
Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
```

```
            180                 185                 190
    Phe Pro Leu Leu Met Trp Ala Trp Lys Ile Ala Pro Ala Leu Val Thr
                195                 200                 205

Gly Asn Thr Val Val Leu Lys Thr Ala Glu Ser Thr Pro Leu Ser Ala
        210                 215                 220

Leu Tyr Val Ser Lys Tyr Ile Pro Gln Ala Gly Ile Pro Pro Gly Val
    225                 230                 235                 240

Ile Asn Ile Val Ser Gly Phe Gly Lys Ile Val Gly Glu Ala Ile Thr
                    245                 250                 255

Asn His Pro Lys Ile Lys Lys Val Ala Phe Thr Gly Ser Thr Ala Thr
                260                 265                 270

Gly Arg His Ile Tyr Gln Ser Ala Ala Ala Gly Leu Lys Lys Val Thr
            275                 280                 285

Leu Glu Leu Gly Gly Lys Ser Pro Asn Ile Val Phe Ala Asp Ala Glu
                290                 295                 300

Leu Lys Lys Ala Val Gln Asn Ile Ile Leu Gly Ile Tyr Tyr Asn Ser
    305                 310                 315                 320

Gly Glu Val Cys Cys Ala Gly Ser Arg Val Tyr Val Glu Ser Ile
                    325                 330                 335

Tyr Asp Lys Phe Ile Glu Glu Phe Lys Ala Ala Ser Glu Ser Ile Lys
                340                 345                 350

Val Gly Asp Pro Phe Asp Glu Ser Thr Phe Gln Gly Ala Gln Thr Ser
                355                 360                 365

Gln Met Gln Leu Asn Lys Ile Leu Lys Tyr Val Asp Ile Gly Lys Asn
            370                 375                 380

Glu Gly Ala Thr Leu Ile Thr Gly Gly Glu Arg Leu Gly Ser Lys Gly
    385                 390                 395                 400

Tyr Phe Ile Lys Pro Thr Val Phe Gly Asp Val Lys Glu Asp Met Arg
                    405                 410                 415

Ile Val Lys Glu Glu Ile Phe Gly Pro Val Val Thr Val Thr Lys Phe
                420                 425                 430

Lys Ser Ala Asp Glu Val Ile Asn Met Ala Asn Asp Ser Glu Tyr Gly
            435                 440                 445

Leu Ala Ala Gly Ile His Thr Ser Asn Ile Asn Thr Ala Leu Lys Val
        450                 455                 460

Ala Asp Arg Val Asn Ala Gly Thr Val Trp Ile Asn Thr Tyr Asn Asp
    465                 470                 475                 480

Phe His His Ala Val Pro Phe Gly Gly Phe Asn Ala Ser Gly Leu Gly
                    485                 490                 495

Arg Glu Met Ser Val Asp Ala Leu Gln Asn Tyr Leu Gln Val Lys Ala
                500                 505                 510

Val Arg Ala Lys Leu Asp Glu
            515

<210> SEQ ID NO 7
<211> LENGTH: 29
<212> TYPE: DNA
<213> ORGANISM: Artificial Sequence
<220> FEATURE:
<223> OTHER INFORMATION: Synthetic (forward primer 1)

<400> SEQUENCE: 7
aaacatatga aataaaaat tttagtaga                                         29

<210> SEQ ID NO 8
```

```
<211> LENGTH: 29
<212> TYPE: DNA
<213> ORGANISM: Artificial Sequence
<220> FEATURE:
<223> OTHER INFORMATION: Synthetic (reverse primer 1)

<400> SEQUENCE: 8
aaactcgagt ttgtgataat atctctcat                                         29

<210> SEQ ID NO 9
<211> LENGTH: 29
<212> TYPE: DNA
<213> ORGANISM: Artificial Sequence
<220> FEATURE:
<223> OTHER INFORMATION: Synthetic (forward primer 2)

<400> SEQUENCE: 9
aaacatatgt cactaatgga caattggaa                                         29

<210> SEQ ID NO 10
<211> LENGTH: 29
<212> TYPE: DNA
<213> ORGANISM: Artificial Sequence
<220> FEATURE:
<223> OTHER INFORMATION: Synthetic (reverse primer 2)

<400> SEQUENCE: 10
aaactcgaga tattttgtct tcactgttc                                         29

<210> SEQ ID NO 11
<211> LENGTH: 29
<212> TYPE: DNA
<213> ORGANISM: Artificial Sequence
<220> FEATURE:
<223> OTHER INFORMATION: Synthetic (forward primer 3)

<400> SEQUENCE: 11
aaacatatga agcagaatt caagcgtaa                                          29

<210> SEQ ID NO 12
<211> LENGTH: 29
<212> TYPE: DNA
<213> ORGANISM: Artificial Sequence
<220> FEATURE:
<223> OTHER INFORMATION: Synthetic (reverse primer 3)

<400> SEQUENCE: 12
aaactcgaga gcctttcgtt ccggcaccg                                         29

<210> SEQ ID NO 13
<211> LENGTH: 615
<212> TYPE: DNA
<213> ORGANISM: Bacillus subtilis

<400> SEQUENCE: 13
atgaaagcag aattcaagcg taaaggaggg ggcaaagtga aactcgttgt cggaatgaca        60
ggggcaacag ggccattttt cggggtcagg ctgctgcagt ggctgaaggc cgccggagtg       120
gaaacccatc tcgttgtgtc tccttgggca aacgtcacga tcaaaacgag aacaggctat       180
acgttacaag aagtagaaca actggccaca tacacttact cacataagga tcaggcggca       240
gccatttcaa gcgggtcgtt tgataccgat ggaatgattg ttgcgccgtg cagcatgaaa       300
tctctcgcaa gcattcgcac aggaatggcg gataatctgc tgacacgtgc ggcggatgtc       360
atgctcaagg agagaaaaaa actcgtcctc ttaacgagag agacgccttt gaaccaaatt       420
```

```
catctcgaaa atatgctagc gcttacgaaa atgggcacca tcattcttcc tccgatgccg    480
gcattttata atcggccgag aagcttagag gaaatggttg accatattgt ttttagaacg    540
ttggaccaat tcggcattcg gcttcctgaa gcgaagcgct ggaatgggat tgaaaaacaa    600
aaaggaggag cttga                                                     615
```

<210> SEQ ID NO 14
<211> LENGTH: 204
<212> TYPE: PRT
<213> ORGANISM: Bacillus subtilis

<400> SEQUENCE: 14

```
Met Lys Ala Glu Phe Lys Arg Lys Gly Gly Lys Val Lys Leu Val
1               5                   10                  15

Val Gly Met Thr Gly Ala Thr Gly Ala Ile Phe Gly Val Arg Leu Leu
            20                  25                  30

Gln Trp Leu Lys Ala Ala Gly Val Glu Thr His Leu Val Val Ser Pro
        35                  40                  45

Trp Ala Asn Val Thr Ile Lys His Glu Thr Gly Tyr Thr Leu Gln Glu
    50                  55                  60

Val Glu Gln Leu Ala Thr Tyr Thr Tyr Ser His Lys Asp Gln Ala Ala
65                  70                  75                  80

Ala Ile Ser Ser Gly Ser Phe Asp Thr Asp Gly Met Ile Val Ala Pro
                85                  90                  95

Cys Ser Met Lys Ser Leu Ala Ser Ile Arg Thr Gly Met Ala Asp Asn
            100                 105                 110

Leu Leu Thr Arg Ala Ala Asp Val Met Leu Lys Glu Arg Lys Lys Leu
        115                 120                 125

Val Leu Leu Thr Arg Glu Thr Pro Leu Asn Gln Ile His Leu Glu Asn
    130                 135                 140

Met Leu Ala Leu Thr Lys Met Gly Thr Ile Ile Leu Pro Pro Met Pro
145                 150                 155                 160

Ala Phe Tyr Asn Arg Pro Arg Ser Leu Glu Glu Met Val Asp His Ile
                165                 170                 175

Val Phe Arg Thr Leu Asp Gln Phe Gly Ile Arg Leu Pro Glu Ala Lys
            180                 185                 190

Arg Trp Asn Gly Ile Glu Lys Gln Lys Gly Gly Ala
        195                 200
```

<210> SEQ ID NO 15
<211> LENGTH: 1422
<212> TYPE: DNA
<213> ORGANISM: Bacillus subtilis

<400> SEQUENCE: 15

```
atggcttatc aagatttcag agaatttctc gctgcccttg aaaaagaagg acagctgctt     60
acagtgaatg aagaggtaaa gccggaaccg gatttagggg cctccgcacg ggcagccagc    120
aatcttggcg ataaaagccc tgcgctctta tttaacaaca tttacggcta tcataacgcg    180
cgaattgcga tgaatgtcat cggctcttgg ccaaaccatg ccatgatgct gggcatgccg    240
aaagacacac cggtaaaaga acagtttttt gaattcgcaa agcgttatga ccagtttccg    300
atgccggtca acgtgaggaa acagcgccaa tttcatgaaa atgaaatcac agaagatatc    360
aatttgttcg atatactgcc tcttttcaga attaaccagg gtgatggagg ctactattta    420
gacaaagcat gtgtcatttc ccgtgatctt gaggaccctg acaacttcgg caaacaaaat    480
```

-continued

```
gtcggcattt acagaatgca agtcaaagga aaagaccgcc ttggcattca gcctgtcccg    540
cagcacgata ttgcaatcca tctgcgccaa gctgaagaac gcggcatcaa ccttccggtc    600
actattgcgc tcggctgtga gccggtcatt acaacggcgg catcgactcc gcttctctat    660
gatcaatcag aatacgaaat ggcaggtgcg attcaaggcg aaccatatcg catcgtcaaa    720
tcaaagctgt ctgatcttga tgttccgtgg ggcgctgaag tggtgcttga aggtgagatt    780
attgccggag agcgcgaata tgaagggccg ttcggtgaat tcacaggcca ttattccggc    840
ggacgcagca tgccgattat caaaattaaa cgcgtctatc acagaaacaa tccgatcttt    900
gaacatttat acttaggcat gccttggaca gaatgcgatt acatgatcgg cattaacaca    960
tgcgtgccgc tttatcagca gttaaaagaa gcgtatccga acgaaattgt ggcagtgaac   1020
gccatgtaca cacacggttt aatcgcgatt gtttccacaa aaacccgcta tggcggattt   1080
gcgaaagcgg tcggcatgcg cgcactcaca acgccgcacg gactcggcta ctgcaaaatg   1140
gtcatagtcg ttgatgagga tgtcgatcca ttcaaccttc gcaggtcat gtgggcgctt   1200 tcgaccaaaa tgcatccgaa acatgatgcg gtcatcattc cggacttatc tgtcctgccg   1260
cttgatccgg gatccaatcc atcaggaatc actcacaaaa tgattctcga cgccactaca   1320
ccggttgcgc cggaaacaag aggccattat tcacagccgc ttgattctcc gctaacaacg   1380
aaagaatggg aacaaaaact aatggactta atgaataaat aa                      1422
```

<210> SEQ ID NO 16
<211> LENGTH: 473
<212> TYPE: PRT
<213> ORGANISM: Bacillus subtilis

<400> SEQUENCE: 16

```
Met Ala Tyr Gln Asp Phe Arg Glu Phe Leu Ala Ala Leu Glu Lys Glu
  1               5                  10                  15

Gly Gln Leu Leu Thr Val Asn Glu Glu Val Lys Pro Glu Pro Asp Leu
             20                  25                  30

Gly Ala Ser Ala Arg Ala Ala Ser Asn Leu Gly Asp Lys Ser Pro Ala
         35                  40                  45

Leu Leu Phe Asn Asn Ile Tyr Gly Tyr His Asn Ala Arg Ile Ala Met
     50                  55                  60

Asn Val Ile Gly Ser Trp Pro Asn His Ala Met Met Leu Gly Met Pro
 65                  70                  75                  80

Lys Asp Thr Pro Val Lys Glu Gln Phe Glu Phe Ala Lys Arg Tyr
                 85                  90                  95

Asp Gln Phe Pro Met Pro Val Lys Arg Glu Glu Thr Ala Pro Phe His
                100                 105                 110

Glu Asn Glu Ile Thr Glu Asp Ile Asn Leu Phe Asp Ile Leu Pro Leu
            115                 120                 125

Phe Arg Ile Asn Gln Gly Asp Gly Gly Tyr Tyr Leu Asp Lys Ala Cys
        130                 135                 140

Val Ile Ser Arg Asp Leu Glu Asp Pro Asp Asn Phe Gly Lys Gln Asn
145                 150                 155                 160

Val Gly Ile Tyr Arg Met Gln Val Lys Gly Lys Asp Arg Leu Gly Ile
                165                 170                 175

Gln Pro Val Pro Gln His Asp Ile Ala Ile His Leu Arg Gln Ala Glu
            180                 185                 190

Glu Arg Gly Ile Asn Leu Pro Val Thr Ile Ala Leu Gly Cys Glu Pro
        195                 200                 205
```

Val Ile Thr Thr Ala Ala Ser Thr Pro Leu Leu Tyr Asp Gln Ser Glu
    210                 215                 220

Tyr Glu Met Ala Gly Ala Ile Gln Gly Glu Pro Tyr Arg Ile Val Lys
225                 230                 235                 240

Ser Lys Leu Ser Asp Leu Asp Val Pro Trp Gly Ala Glu Val Val Leu
                245                 250                 255

Glu Gly Glu Ile Ile Ala Gly Glu Arg Glu Tyr Glu Gly Pro Phe Gly
            260                 265                 270

Glu Phe Thr Gly His Tyr Ser Gly Gly Arg Ser Met Pro Ile Ile Lys
        275                 280                 285

Ile Lys Arg Val Tyr His Arg Asn Asn Pro Ile Phe Glu His Leu Tyr
    290                 295                 300

Leu Gly Met Pro Trp Thr Glu Cys Asp Tyr Met Ile Gly Ile Asn Thr
305                 310                 315                 320

Cys Val Pro Leu Tyr Gln Gln Leu Lys Glu Ala Tyr Pro Asn Glu Ile
                325                 330                 335

Val Ala Val Asn Ala Met Tyr Thr His Gly Leu Ile Ala Ile Val Ser
            340                 345                 350

Thr Lys Thr Arg Tyr Gly Gly Phe Ala Lys Ala Val Gly Met Arg Ala
        355                 360                 365

Leu Thr Thr Pro His Gly Leu Gly Tyr Cys Lys Met Val Ile Val Val
    370                 375                 380

Asp Glu Asp Val Asp Pro Phe Asn Leu Pro Gln Val Met Trp Ala Leu
385                 390                 395                 400

Ser Thr Lys Met His Pro Lys His Asp Ala Val Ile Ile Pro Asp Leu
                405                 410                 415

Ser Val Leu Pro Leu Asp Pro Gly Ser Asn Pro Ser Gly Ile Thr His
            420                 425                 430

Lys Met Ile Leu Asp Ala Thr Thr Pro Val Ala Pro Glu Thr Arg Gly
        435                 440                 445

His Tyr Ser Gln Pro Leu Asp Ser Pro Leu Thr Thr Lys Glu Trp Glu
    450                 455                 460

Gln Lys Leu Met Asp Leu Met Asn Lys
465                 470

<210> SEQ ID NO 17
<211> LENGTH: 228
<212> TYPE: DNA
<213> ORGANISM: Bacillus subtilis

<400> SEQUENCE: 17
atgcatacat gtcctcgatg cgactcaaaa aagggagaag tcatgagcaa atcgcctgta      60
gaaggcgcat gggaagttta tcagtgccaa acatgctttt ttacatggag atcctgtgaa     120
ccggaaagca ttacaaatcc cgaaaaatac aatccagcgt ttaaaattga tccaaggaa      180 acagaaacag caattgaagt tccggcggtg ccggaacgaa aggcttga                 228

<210> SEQ ID NO 18
<211> LENGTH: 75
<212> TYPE: PRT
<213> ORGANISM: Bacillus subtilis

<400> SEQUENCE: 18

Met His Thr Cys Pro Arg Cys Asp Ser Lys Lys Gly Glu Val Met Ser
1               5                   10                  15

```
Lys Ser Pro Val Glu Gly Ala Trp Glu Val Tyr Gln Cys Gln Thr Cys
             20                  25                  30

Phe Phe Thr Trp Arg Ser Cys Glu Pro Glu Ser Ile Thr Asn Pro Glu
             35                  40                  45

Lys Tyr Asn Pro Ala Phe Lys Ile Asp Pro Lys Glu Thr Glu Thr Ala
             50                  55                  60

Ile Glu Val Pro Ala Val Pro Glu Arg Lys Ala
65                   70                  75
```